United States Patent [19]

Aust et al.

[11] Patent Number: 5,180,381
[45] Date of Patent: Jan. 19, 1993

[54] ANTERIOR LUMBAR/CERVICAL BICORTICAL COMPRESSION PLATE

[76] Inventors: Gilbert M. Aust; Timothy E. Taylor, both of 100 Washington St. Ste. 204, Huntsville, Ala. 35801

[21] Appl. No.: 765,014

[22] Filed: Sep. 24, 1991

[51] Int. Cl.⁵ .................. A61B 17/56; A61B 17/58; A61F 2/44
[52] U.S. Cl. ...................................... 606/61; 606/69; 623/17
[58] Field of Search ................... 606/60-61, 606/69-71; 623/17

[56] References Cited

U.S. PATENT DOCUMENTS 3,741,205 6/1973 Markolf et al. .................. 606/61

FOREIGN PATENT DOCUMENTS 2254304 7/1975 France ...................... 606/61

*Primary Examiner*—Ronald Frinks

[57] ABSTRACT

An anterior spinal fixation device which provides an anterior lumbar and cervical fusion fixation system which has numerous advantages over existing anterior, posterior and lateral implant systems. Anterior (access from the patients stomach region) lumbar surgery allows the surgeon to remove the entire intervertebral disc, which is not possible during posterior or lateral surgery. Many interbody fusion operations require removal of disc material, insertion of new graft material and fusion of the adjoining vertebrae. This plate and screw fixation invention provides the ability to perform this function. The novelty of this invention includes an "H" shaped overall design allowing for multiple fusions, a bicortical fixation system which is achieved by inserting four screws at a 45 degree angle into two cortical surfaces. It also provides structural integrity by placing more friction on the screws which allows for increased pull out strength. An anterior fixation device also is further from the spinal cord which reduces the chance of contact with the nerve roots.

2 Claims, 2 Drawing Sheets

ANTERIOR LUMBAR/CERVICAL BICORTICAL COMPRESSION PLATE

BACKGROUND OF INVENTION

This invention relates to an anterior lumbar and cervical interbody fusion system that is installed on the anterior portion of the spine and serves to mechanically fuse vertebral bodies.

The evolution of daily physical demands on the human body have continued to decrease in the workplace due to great advances in industrial automation. Most jobs today involve sitting for long periods of time. During relaxed sitting, the loads on the lumbar spine are greater than during upright standing. Thus, our "sitting" work style and active sports during our leisure time have significantly increased the amount of spinal problems. Loads on the spine are produced primarily by body weight, muscle activity, and externally applied loads. Since the lumbar region is the main load bearing area of the spine, and the area where pain most commonly occurs, lumbar as well as cervical spinal surgery has become a demanding and growing field of surgery. Also as a result of aging, and a more recreationally active population, the number of spinal fusions performed in the United States has grown significantly.

The objective of spinal implants is to facilitate fusion of elements of the spine. This invention addresses this issue.

The percentage of spinal fusions (using spinal implants) has increased over the past few years but is still less than 50%. Most spinal fusions are actually candidates for spinal implants.

The spinal implant market has been the most rapidly growing segment of the orthopedic market in recent years.

The primary factors responsible for the strong growth in the use of spinal implants are innovations in the design of spinal implant devices, changing physician attitudes toward the use of such devices, and the growing number of orthopedic surgeons trained in the use of such implants.

Spinal fusions are performed to treat degenerative diseases, deformities, and trauma, but until recently, surgeons had limited implant options for treating spinal conditions. Physicians treating spinal conditions either did so without implants, or utilized basic implant devices. These devices did not, however, provide the patient with sufficient structural stability, and the fusion system and efficacy were limited.

In seeking better alternatives for spinal fusions, physicians began to use plates and screws designed primarily for use on bones in other areas of the body. Due to the perceived risk of paralysis, spinal implants were slow to become popular among physicians. Now various plate, rod and screw implants have been specifically designed for the spinal region and the efficacy of these implants have been proven. Clinical studies have shown that surgeries using spinal implants are more effective at providing structure and rigidity to the spine than surgeries in which implants are not used.

This invention is an continuation in this area of development and provides for the first time an anterior lumbar and cervical fusion fixation system which has numerous advantages over posterior and lateral spinal implant systems.

Anterior (access from the patients stomach region) lumbar and cervical surgery allows the surgeon to remove the entire intervertebral disc, which is not possible during posterior or lateral surgery. Spinal fusion operations require removal of disk material, insertion of new graft material and mechanical fusion of the adjoining vertebrae.

Surgical operations performed to date do not allow the surgeon the means to keep the graft material in place nor does it allow the surgeon the ability of evenly distributing the loads on the graft material. The proposed anterior fusion procedure with an anterior plate captures both of these task.

Posterior and lateral fusion and fixation operations do not allow the surgeon total access to the vertebral inner disc and does not provide a fixation device that eliminates all bending moments.

Not having direct access to the intervertebral disk, the surgeon is unable to extract the entire disk which when inserting the graft material creates additional problems and may not remedy the problem disc. Posterior and lateral spinal operations involve working closer to the spinal cord than do anterior operations. The extra clearance gained by anterior surgery significantly reduces the chance of disrupting the spinal cord and electrical impulses.

This invention allows the surgeon full access to the vertebral intervertebral disc and once installed, the fixation device is installed closer to the center of rotational moment which significantly reduces the bending moment loads on the spine.

One object of the invention is to provide an anterior fusion mechanical fixation device that allows the surgeon full access to the intervertebral disc.

Another object of the invention is the provision of a fixation device that eliminates the need for post operative body jackets.

Yet another object of the invention is the provision for a mechanical fixation device that provides a restraint for the implanted graft material so the chance for displacement of the disc graft material is significantly reduced.

Yet another object of this invention is to provide a better mechanical stabilization method that is biomechanically sound and eliminates bending moments in the vertebral bodies.

The novelty and key to this system is bicortical fixation systems which allows the surgeon to install four screws into two cortical bone surfaces at roughly a 45 degree angle. No other system employs such a design and for the first time creates a significantly increased pullout strength and safety factor. Mechanical advantages include increased screw friction which reduces the risk of screw pull out, moment arm stress reduction due to closeness of fixation system to center line of rotation, ability to use smaller fixation screw hardware thus allowing smaller holes in the bone and compression device which pull the two vertebral bodies together to insure bone grafting stabilization.

SUMMARY OF THE INVENTION

In accordance with our invention, we overcome the above difficulties by providing an anterior lumbar and cervical fixation device that allows the surgeon full access to the disk area, a fixation system that captures two cortical surfaces via a 45 degree angle screw insertion, a fixation system that pulls the two vertebral bodies closer together insuring a tight fusion, a fixation point closer to the center of rotation to reduce torsional loads and provides a physical barrier to reduce the chance of displacement of the graft material.

The materials used to provide the basic design are FDA approved human implant metals such as 316L stainless steel, titanium, titanium-vanadium-aluminum and cobalt-chromium-molybdenum.

The surgical process involves removing the patient's intervertebral disc, inserting the bone graft material to replace the extracted disc, pre-drilling 4 pilot screw holes on a 45 degree angle-penetrating both cordices of the vertebra, and installing the plate with 3.5 mm or 4.5 mm cortical or cancellous screws.

DESCRIPTION OF DRAWINGS

A typical fixation device embodying features of our invention is illustrated in the accompanying drawing form part of this application in which.

DETAILED DESCRIPTION

Figure 1:
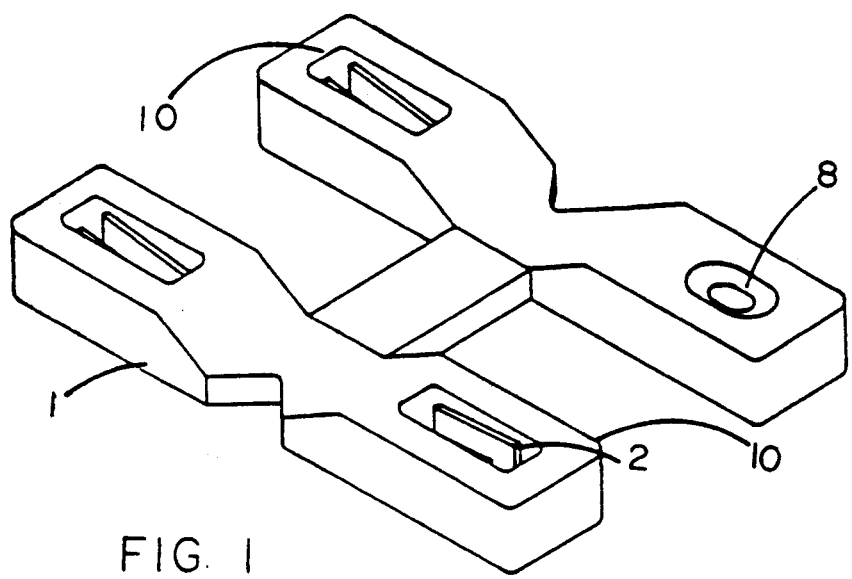
FIG. 1 is a perspective view showing the typical fixation device.

As shown in the drawings, the preferred lumbar fixation device in accordance with the present invention includes a fixation plate 1 which is comprised of FDA approved metal implant material. Overall dimensions of plate 1 are 27 mm in width, 52 mm in length and 1-5 mm thick. There are four slotted screw holes or four counter sunk holes for installing the plate onto the spine. These stainless steel cortical or cancellous screws have round hex heads and rest on a sloping compression shelf 2 or counter sunk hole 8 which distributes the loads to both cortical bone surfaces in the required manner.

Figure 3:
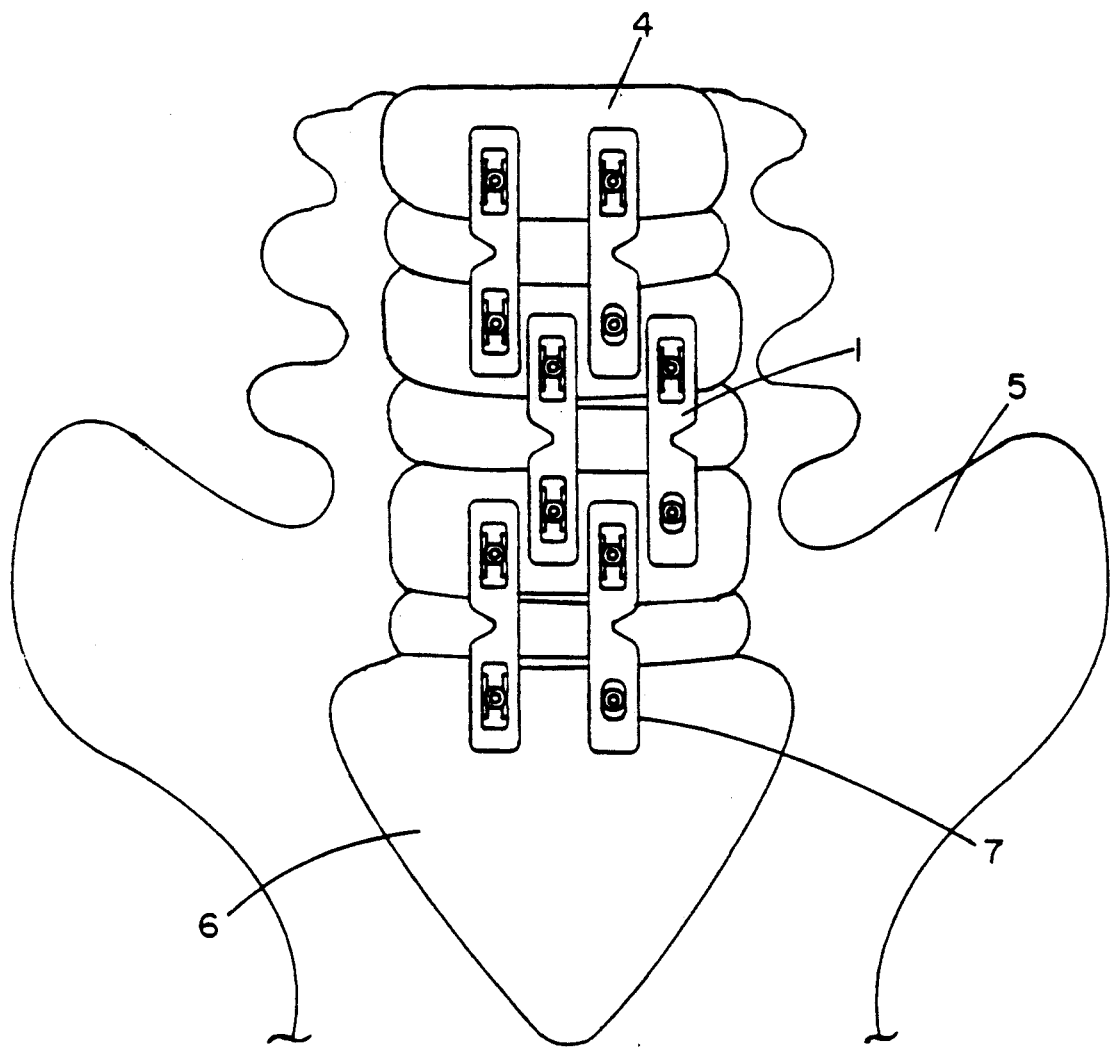
FIG-3 is a front (anterior) view of the lumbar/pelvic area showing three fixation devices installed on L3, L4,. L5 and S1. Plate 7 is different than the other lumbar plates due to the angle and configuration of the sacrum.

The plate 1 has opposite ends which are bifurcated at each end of the plate to form a pair of spaced generally parallel legs 10. The legs 10 are spaced apart a distance greater than the width of the legs so that the leg of another fixation device can be positioned between them, as shown in FIG. 3.

The legs 10 are provided with screw seats 2 adjacent to the holes 8, with the screw seats 2 being so positioned that when a screw in inserted into the hole 8 and the screw head seated on the screw seat 2 the screw will extend from the plane of the plate at an angle of about 45°.

It can readily be seen that the plate with the legs 10 is in the form of a letter H.

Figure 2:
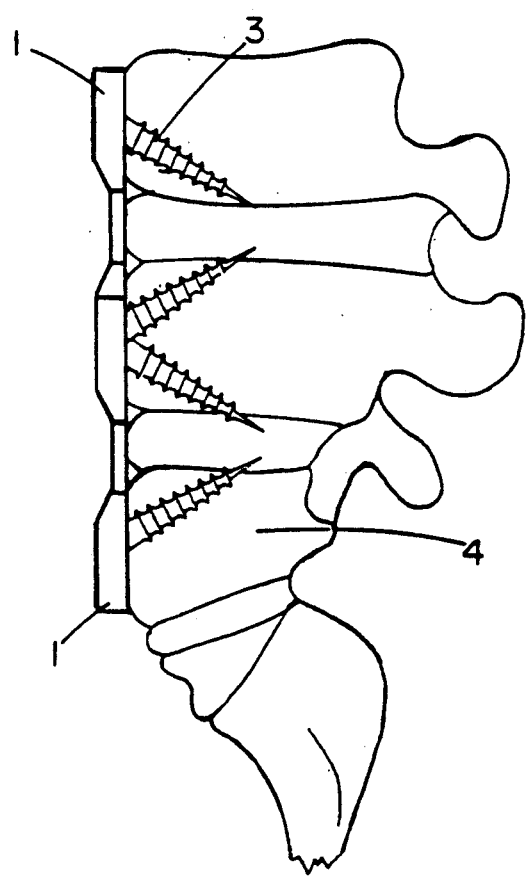
FIG. 2 is a side view of the lower spine (lumbar) region with two fixation devices installed with cortical screws on lumbars-L4 and L5.

FIG. 2 depicts a side view of the lower spine which includes the vertebral bodies and the sacrum and shows the aforementioned screws 3 in place along with two fixation plates 1. FIG. 3 shows a front (anterior) view of the lumbar/pelvic region 4, 5, 6 with three fixation plates 1 installed on vertebral bodies L3, L4 and L5. Fixation plate 7 is shown installed on the L5-S1 interface.

Since various changes and modifications of the invention will occur to those skilled in the art within the spirit of the invention, the invention is not to be taken as limited except by the scope of the appended claims. Depending on the purpose of the fixation device it is reasonable to think that one might want to vary the materials to use other FDA approved metals such as titanium, titanium-vanadium-aluminum or cobalt-chromium-molybdenum as well as change the basic shape.

What is claimed is:

1. A spinal fixation device, comprising a substantially flat plate having opposite ends, said ends being bifurcated to form a pair of spaced generally parallel legs on said ends, said pairs of legs extending away from each other in opposite directions, each of said legs having therein an opening for receiving a screw, said legs being provided with screw seats adjacent to said openings, said screw seats being so positioned that when a screw is inserted into one of said openings and the head of the screw is seated on the screw seat the screw extends from the plane of said plate at an angle of about 45°.

2. The device of claim 1 wherein the device is H-shaped, said legs on each end of the plate being spaced apart a distance greater than the width of the legs such that the leg of another fixation device can be positioned between the legs of each pair of legs.

* * * * *